(12) United States Patent
Kruth et al.

(10) Patent No.: US 8,590,157 B2
(45) Date of Patent: Nov. 26, 2013

(54) PROCEDURE FOR DESIGN AND PRODUCTION OF IMPLANT-BASED FRAMEWORKS FOR COMPLEX DENTAL PROSTHESES

(75) Inventors: Jean-Pierre Kruth, Heverlee (BE); Ignace Naert, Holsbeek (BE); Ben Vandenbroucke, Waregem (BE)

(73) Assignee: Layerwise N.V., Heverlee (BE)

(*) Notice: Subject to any disclaimer, the term of this patent is extended or adjusted under 35 U.S.C. 154(b) by 1517 days.

(21) Appl. No.: 11/795,897

(22) PCT Filed: Jan. 25, 2006

(86) PCT No.: PCT/BE2006/000005
§ 371 (c)(1),
(2), (4) Date: Jul. 24, 2007

(87) PCT Pub. No.: WO2006/079188
PCT Pub. Date: Aug. 3, 2006

(65) Prior Publication Data
US 2008/0206710 A1   Aug. 28, 2008

(30) Foreign Application Priority Data
Jan. 25, 2005   (GB) .................. 0501464.2

(51) Int. Cl.
*A61C 8/00* (2006.01)
*G06F 19/00* (2011.01)
*G06F 17/50* (2006.01)

(52) U.S. Cl.
USPC ......... 29/896.1; 29/557; 433/174; 433/201.1; 700/98; 700/118; 700/119; 703/1

(58) Field of Classification Search
USPC .............. 249/54; 264/16; 433/223, 174, 218, 433/225, 213; 700/118, 163, 98, 159; 75/955; 29/896.1, 557; 219/121.66, 219/121.65, 121.83; 703/1
See application file for complete search history.

(56) References Cited

U.S. PATENT DOCUMENTS

| | | | | |
|---|---|---|---|---|
| 4,571,187 A | * | 2/1986 | Weissman | 433/221 |
| 4,713,005 A | * | 12/1987 | Marshall et al. | 433/180 |
| 4,957,439 A | * | 9/1990 | Shoher et al. | 433/180 |
| 5,768,134 A | * | 6/1998 | Swaelens et al. | 700/121 |
| 5,823,778 A | * | 10/1998 | Schmitt et al. | 433/214 |
| 5,963,775 A | * | 10/1999 | Fang | 419/36 |
| 6,325,961 B1 | * | 12/2001 | Beers et al. | 264/401 |
| 6,682,688 B1 | * | 1/2004 | Higashi et al. | 264/497 |
| 6,791,057 B1 | * | 9/2004 | Kratzsch et al. | 219/121.63 |

(Continued)

FOREIGN PATENT DOCUMENTS

| | | |
|---|---|---|
| DE | 10300301 | 7/2004 |
| EP | 1364625 | 11/2003 |
| WO | WO2004/075771 | 9/2004 |

OTHER PUBLICATIONS

Pandey, "Improvement of surface finish by staircase machining in fused deposition model," Dec. 2001, pp. 323-331.*

(Continued)

*Primary Examiner* — Alexander P Taousakis
(74) *Attorney, Agent, or Firm* — Bacon & Thomas, PLLC (57) ABSTRACT

The present invention provides methods allowing the use of selective laser powder processing techniques for the production of medically acceptable prosthetic dental frameworks. The frameworks produced according to the present invention have high grade mechanical properties as well as a high accuracy.

19 Claims, 6 Drawing Sheets

(56) References Cited

U.S. PATENT DOCUMENTS

| | | | |
|---|---|---|---|
| 7,080,979 B2* | 7/2006 | Rubbert et al. | 433/24 |
| 7,780,907 B2* | 8/2010 | Schmidt et al. | 419/6 |
| 7,950,924 B2* | 5/2011 | Brajnovic | 433/75 |
| 8,021,154 B2* | 9/2011 | Holzner et al. | 433/223 |
| 2001/0036617 A1* | 11/2001 | Karmaker et al. | 433/173 |
| 2002/0102517 A1* | 8/2002 | Poirier | 433/173 |
| 2002/0187458 A1* | 12/2002 | Dolabdjian et al. | 433/218 |
| 2004/0031780 A1* | 2/2004 | Hagemeister et al. | 219/121.85 |
| 2004/0133298 A1* | 7/2004 | Toyserkani et al. | 700/166 |
| 2004/0158342 A1* | 8/2004 | Wolf et al. | 700/98 |
| 2004/0197737 A1* | 10/2004 | Uckelmann et al. | 433/173 |
| 2006/0093988 A1* | 5/2006 | Swaelens et al. | 433/76 |
| 2006/0212154 A1* | 9/2006 | Von Schroeter et al. | 700/118 |

OTHER PUBLICATIONS

Choi et al, "Modelling and optimisation of Rapid Prototyping," Aug. 18, 2001.*

Kruth et al, "Rapid Manufacturing of Dental Prostheses by means of Selective Laser Sintering/Melting," Sep. 28, 2005.*

Office Action issued in EP 06 705 053.4, Apr. 18, 2011, 6 pages.

Official Communication from the European Patent Office (EPC) for European Patent Application 06705053.4, dated May 8, 2012 (5 pages).

* cited by examiner

PROCEDURE FOR DESIGN AND PRODUCTION OF IMPLANT-BASED FRAMEWORKS FOR COMPLEX DENTAL PROSTHESES

FIELD OF THE INVENTION

The present invention relates to frameworks for dental prostheses produced using selective laser powder processing techniques as well as to a method for the production of such frameworks.

BACKGROUND OF THE INVENTION

Figure 1:
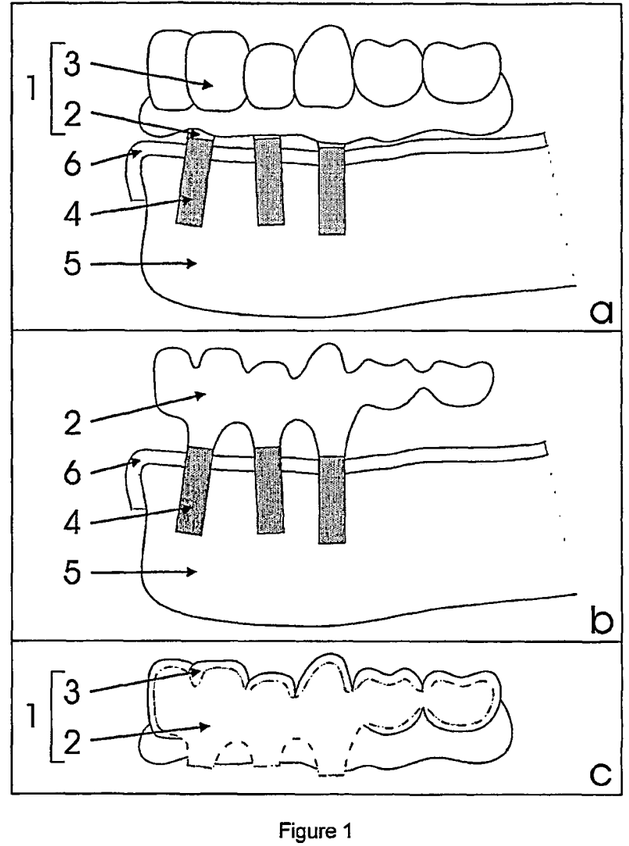
FIG. 1: Implant-based prosthesis: (a) Left view drawing of section of lower jaw with implant supported prosthesis (b) Left view drawing of the framework without teeth (c) Transparency left view drawing of prosthesis. (1) prosthesis, (2) framework, (3) teeth, (4) oral implants, (5) jawbone and (6) soft tissue.

A framework for a dental prosthesis (FIG. 1) (2) is the metal base structure of the prosthesis (1). It is supported by oral implants (4) placed in the jawbone (5) or by remaining teeth. Such framework is fixed to the jaw by screwing it on the implants or by cementing it on the remaining teeth. The framework supports the missing teeth (3) which are attached on the support surfaces on top of the framework. The prostheses are patient specific and have to meet strict requirements of accuracy to reach an optimal fit at the prosthesis-implant or prosthesis-tooth junction. To distribute forces evenly and to avoid high stresses in the jawbone causing the oral implants to loose and to diminish the risk for colonization of bacteria resulting in infection and eventually bone loss, a good passive fit between the framework and the implants or the remaining teeth and severe fit criteria below 40 µm are necessary. Because the framework can replace all teeth and because the framework connects the occlusal surfaces of the missing teeth with the oral implants, the framework is larger and more massive in comparison with other dental applications like crowns and small bridges.

The conventional commercial systems to produce these frameworks are based on a manual design of a physical model of the framework and a production by means of lost wax casting or milling. Although these processes lead to high precision, they are time consuming and inefficient. The lost wax method is a lengthy and labour-intensive process and comprises many manual steps (fabricating the wax pattern, embedding the wax pattern, burning out the wax material, metal casting, post-processing). By digitizing the manual design and using CAM-instructions, the frameworks can be produced through a milling process. However, this milling process is also time consuming because of the lengthy calculation of the tool paths and because of the lengthy manual finishing needed to obtain an accurate fit of the framework. Moreover, most of the material is wasted and spatial restrictions limit the production of complex shapes.

WO2004075771 provides a method for the digital design of a model of the framework. This digital model is subsequently used in rapid prototyping techniques to generate moulds, which can be used for indirect production of the final framework. Alternatively, it is proposed in WO2004075771 to use said digital model of the framework together with CAM-instructions to directly produce the framework by automated milling.

The present invention describes for the first time the direct rapid manufacturing of medically acceptable frameworks produced using computer controlled selective laser powder processing techniques (SLPP). The accuracy of the biocompatible frameworks meets the required severe fit criteria and their high density guarantees highgrade mechanical properties which can resist the complex and heavy loading conditions and long term wear to which a large, implant-supported framework is subjected. Selective laser powder processing techniques have the advantage over conventional methods for the production of dental frameworks that they allow to fabricate complex shapes without the need for lengthy manual pre- or post-processing and have the possibility of mass customization. As Selective laser powder processing techniques allow to produce many different geometries in a single production run, many different frameworks, adapted to the respective patient geometries and requirements, can be produced at the same time without manual intervention.

SUMMARY OF THE INVENTION

It is a first object of the present invention to provide a method for the production of a dental prosthetic framework having a density higher than 97%, more preferably higher than 99%, wherein said framework is directly produced in a biocompatible material using a selective laser powder processing technique. The frameworks produced according to the present invention typically comprises at least one fitting structure for the installation of the framework on a supporting implant, more preferably the framework comprises more than two fitting structures, even more preferably more than 3. In a preferred embodiment the mean gap size between the fitting planes of the fitting structures of said framework and the supporting implants is below 40 µm.

In a second object the present invention provides dental prosthesis comprising a framework directly produced using a selective laser powder processing technique.

DETAILED DESCRIPTION OF THE INVENTION

Definitions

"Selective Laser Powder Processing or SLPP" refers to a layer-wise manufacturing technique that allows generating complex 3D parts by selectively consolidating successive layers of powder material on top of each other using thermal energy supplied by a focused laser beam. SLPP includes the processing of various types of powder with different types of material (plastic, metal, ceramic) and powder composition (single component powder grains, composite powder grains, mixture of powder grains). Different binding mechanisms can be responsible for the consolidating of the powder: solid state sintering, chemically induced binding, liquid phase sintering, partial melting, full melting (see reference below). The thermal energy supplied by the laser beam can be added to the powder in a second step after the deposition of a powder layer in the first step, or the deposition and consolidating of the powder can be combined in a single step. Selective Laser Powder Processing comprises amongst other the following techniques: selective laser sintering, selective laser full melting and laser cladding. An overview of Selective Laser Powder Processing techniques is presented in J. P. Kruth, et al., Binding mechanisms in selective laser sintering and selective laser melting, Proceedings of 15$^{th}$ annual Solid Freeform Fabrication Symposium, Austin, Aug. 2-4, 2004.

DESCRIPTION

The currently used methods for the production of frameworks, such as lost wax casting and milling, are lengthy and labour intensive processes, and do not allow for allow mass customisation. The present invention provides methods allowing the use of selective laser powder processing techniques for the production of medically acceptable prosthetic dental frameworks. These selective laser powder processing techniques have the important advantage that they permit to produce multiple different frameworks, each having a patient specific geometry, within a single production run.

It is an important aspect of the present invention that the developed methods allowed to produce dental frameworks having a density exceeding 97%. This high density guarantees that the frameworks produced according to the present invention have the high grade mechanical properties required for an implant supported framework to resist the complex and heavy loading conditions and long term wear it is subjected to. As far as the applicants are aware the present invention is the first document disclosing complex SLPP produced shapes in a biocompatible material having such high density.

Therefore, in a first object the present invention provides a method for the production of a dental prosthetic framework having a density higher than 97%, more preferably higher than 99%, for instance 99.9%, wherein said framework is directly produced in a biocompatible material using a selective laser powder processing technique. Preferably the biocompatible material is titanium, a titanium-alloy, a cobalt-chromium-alloy or a ceramic. The framework produced according to the present invention typically comprises at least one fitting structure for the installation of the framework on a supporting implant, more preferably the framework comprises more than two fitting structures, even more preferably more than 3. In a preferred embodiment the mean gap size between the fitting planes of the fitting structures of said framework and the supporting implants is below 40 μm.

In a particular embodiment the method of the present invention comprises a first step wherein a digital model of the framework is obtained and a second step wherein the framework is produced according to said digital model using a selective laser powder processing technique. The generation of the digital model of the framework can be achieved in different ways and is dependent on the clinical procedure used. In a first type of clinical procedure (Classical procedure) the framework is designed and produced after the implants are installed in the patient's mouth, while in the second type of clinical procedure (Alternative procedure) the framework is virtually designed as a part of the planning of the surgical intervention, i.e. prior to the installation of the implants in the patient's mouth. When the method of the present invention is integrated in a clinical procedure according to the first type a digital design can be obtained by manually designing a physical model of the framework using a work model representing the patient's jawbone including the installed implants and any remaining teeth. This physical model of the framework can then be digitised in order to obtain a digital model of the framework. It is, however, preferred to use mainly digital methods to obtain the digital model of the framework. Regardless of the clinical procedure the digital generation of the digital model of the framework preferably comprises the following steps:

(i) obtaining the teeth arch geometry, which comprises digital data on (a) the position and geometry of each implant and remaining tooth, on (b) the shape of the teeth arrangement and (c) on the calculated match between said elements, and (ii) designing the digital model of the framework using said teeth arch geometry.

In case the method of the present invention is integrated in a Classical medical procedure the teeth arch geometry is preferably obtained by carrying out following steps (i) measuring the position and geometry of each implant and remaining tooth on a physical work model of the patients jaw bone, said work model being prepared after the installation of the implants in the patients mouth, (ii) preparing a physical teeth arrangement on said work model, (iii) digitising said physical teeth arrangement to obtain a digital 3D teeth model; and (iv) mathematically matching the measurements obtained in step (i) and (iii).

In case the method of the present invention is integrated in the Alternative medical procedure, the teeth arch geometry is obtained as a part of the planning of the surgical intervention. This is preferably done by integrating following steps in said surgical planning:

(i) planning the installation of the implants in the patient's jawbone using a digitised representation of the jawbone and appropriate planning software, (ii) generating a digital 3D teeth model by selecting and positioning virtual teeth on the digitised representation of the jawbone, (iii) deriving the teeth arch geometry out of the digital data generated in steps (i) and (ii).

Once the teeth arch geometry is available the digital model of the framework is preferably designed by applying understanding steps:
(i) obtaining a digital representation of the total tooth surface of each tooth comprised in the digital 3D teeth model,
(ii) calculating a reduction of each tooth surface comprised in the 3D digital teeth model in order to determine the geometry of the surfaces required on the framework to support the respective teeth,
(iii) Designing the fitting structures on the digital framework using the data on the positions and geometries of the implants and remaining teeth, and
(iv) designing the connection between the designed fitting structures (iii) and the in step (ii) calculated support surfaces using the calculated match between the two elements of the teeth arch geometry.

In the SLPP production of a framework according to the present invention it is preferred that the fitting planes of the fitting structures are oriented upwards in the build volume of the SLPP machine in order to optimise the finishing of these planes. Furthermore, it was found that the accuracy of the finishing of the fitting planes was highest when the angles in the build volume of the slopes of the fitting planes differ less than 10° degrees, preferably less than 5°, from an empirically determined optimal angle for minimising the errors related to layer-wise production. Therefore, it is preferred that the framework is positioned under a tilt angle resulting in that the angles in the build volume of the slopes of at least two fitting planes differ less than 10 degrees, preferably less than 5°, from an empirically determined optimal angle for minimising the errors related to layer-wise production. More preferably the framework should be positioned such that all fitting planes differ less than 10°, preferably less than 5°, from said empirically determined optimal angle. However, depending on the patient geometry it is not always possible to position the framework such that all angles of the slopes of the fitting planes are optimally positioned. In these cases the framework is preferably designed and produced such that the fitting structures of which the angle in the build volume of the slopes of the fitting planes differ more than 10° from said empirically determined optimal angle, are designed and produced to comprise extra material extending said fitting structures. The fitting structures comprising extra material are then subsequently subjected to a post processing step during which the extra material is removed to obtain the desired fitting structure lengths and the required slopes of the fitting planes.

In some SLPP techniques, such as selective laser full melting and selective laser cladding, the use of support structures is preferred for the horizontal bottom planes of the framework and for overhanging planes of the framework connected to such bottom planes with an angle lower than 30°. Preferably these support structures linking said overhanging and bottom planes with the basis of the building platform connect with the framework planes via a grid structure in order to facilitate the disconnection of the framework from the supporting structures after the termination of the production run.

The invention is illustrated in more detail below.

The procedure to design and produce a framework according to the present invention varies depending on the preferred clinical procedure. Two main procedures can be discriminated, which are respectively designated as the Classical and Alternative procedure. In the Classical procedure the framework and the prosthesis are designed and fabricated after the installation of the implants in the mouth, while in the Alternative procedure the framework and the prosthesis are designed and produced prior to the installation of the implants in the mouth. Below it is illustrated how the production of a patient specific framework using a selective laser powder processing technique (SLPP) can be integrated in both procedures.

Figure 2:
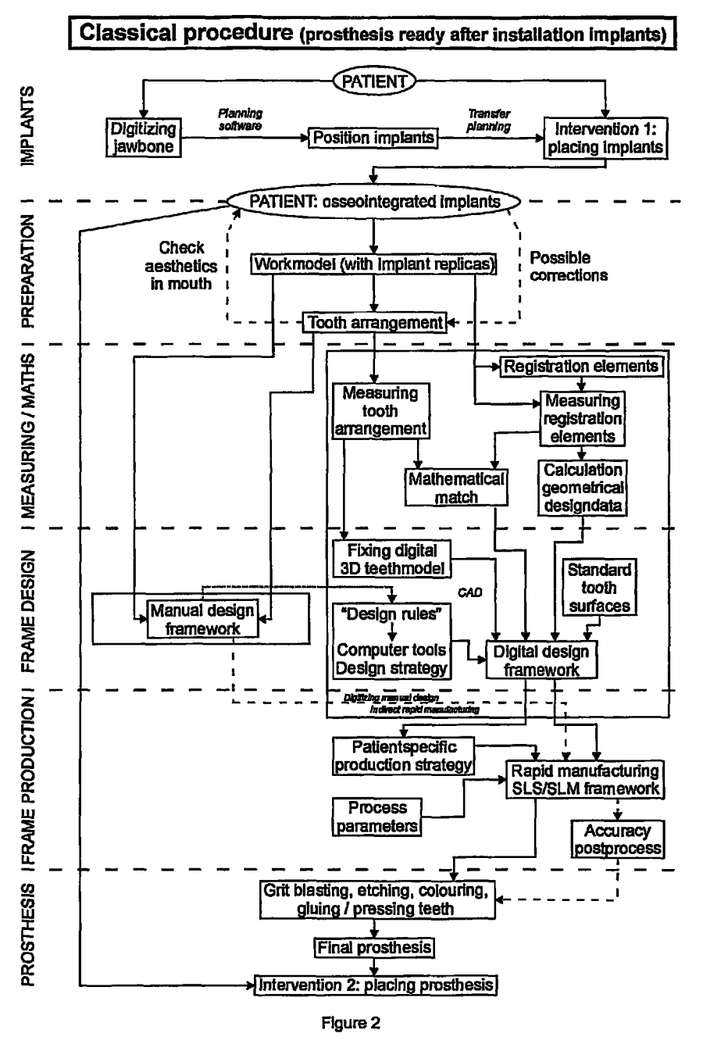
FIG. 2: Scheme representing the design and production of the framework in the Classical clinical procedure

Design and Production of a SLPP Framework in the Classical Procedure (FIG. 2)

A stepwise overview of the design, production and installation of a dental prosthesis made according to the present invention is given for the Classical procedure. This procedure comprises six main steps which are termed: implant installation, preparation, measuring/mathematics, frame design, frame production and prosthesis step (FIG. 2).

1. Implant Installation Step

Based on a digitized representation of the jawbone of the patient an operator chooses the most appropriate positions for the implants by means of planning software. Subsequently, the implants are installed in the patient's jawbone at the planned positions, possibly using a physical tool facilitating the transfer of the planning. After this first medical intervention the implants can start healing in the jawbone.

2. Preparation—Step

Either after a period of osseointegration (delayed loading) or immediately after the installation of the implants (early loading) a work model of the jawbone is prepared. Thereto an elastomer impression is made of the jaw after impression copings are placed on top of the implants in the patient's mouth. The impression copings are retained in the elastomer material and indicate the position of the implants. Thereafter, implant replicas are placed on the impression copings and based on the negative elastomer impression a positive plaster work model is made. This work model is a physical representation of the jawbone of the patient, including remaining teeth, and having implant replicas which reflect the positions of the implants in the jawbone of the patient. Further the operator relates the upper and the lower jawbone model according to well known clinical procedures (site registration).

Upon this work model a teeth arrangement is shaped. This physical teeth arrangement reflects the final prosthesis but does not comprise the internal metal framework. This tooth arrangement allows to check the aesthetics of the prosthesis in the mouth of the patient. The patient can consider some corrections to the teeth arrangement until he/she is satisfied with the final result.

3. Measuring/Mathematics—Step

In this step the teeth arch geometry is measured and calculated. This teeth arch geometry comprises the measured positions and geometry of the implants and possible remaining teeth and the measured shape of the teeth arrangement as well as the mathematical connection between these two measurements. Especially the measurement of the position of the implants has to be very accurate with regard to the final fit between the framework and the implants.

Figure 3:
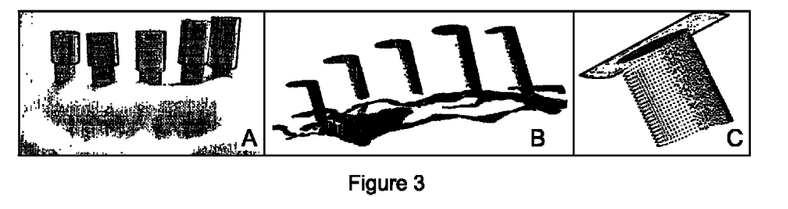
FIG. 3: Measurement of position of implants: (A) Registration elements mounted on implant replicas of work model, (B) Point cloud of registration elements, (C) Fitting of top surface and cylinder of registration element to calculate position and gradient of element.

Preferably the position and geometry of the implants and possible remaining teeth are measured on the plaster work model using measurement equipment that is currently available in a dental lab such as a simple optical scanner or a simple mechanical sensor probe. Alternatively high precision measurement equipment such as an optical probe or/and a co-ordinates measurement machine can be used. When measurements are performed using a simple optical scanner or a simple mechanical sensor probe the use of registration elements is preferred. These elements are mounted on top of the implant replicas of the work model and in that position the elements are measured. There are different possible shapes for the registration elements, such as cylinders, cones, beams and pyramids. FIG. 3a shows an example of cylindrical registration elements mounted on a work model and FIG. 3b shows a point cloud of the registration elements measured with an optical scanner (Laserscan 3D from Willytec GmbH). The measured data is subsequently processed to calculate the position and inclination of each of the registration elements, using numerical methods and the known dimensions of the registration elements. (FIG. 3c).

As mentioned, it occurs that the framework is supported not only by implants but also by remaining teeth. The position and geometry of these are also measured on the plaster work model. The determination of the position and geometry of the remaining teeth should be accurate, however deviations below 0.1 mm are acceptable as the fixation of the framework on the remaining teeth is done by cementing and the geometry of the remaining teeth can be adapted by a tool.

Figure 4:
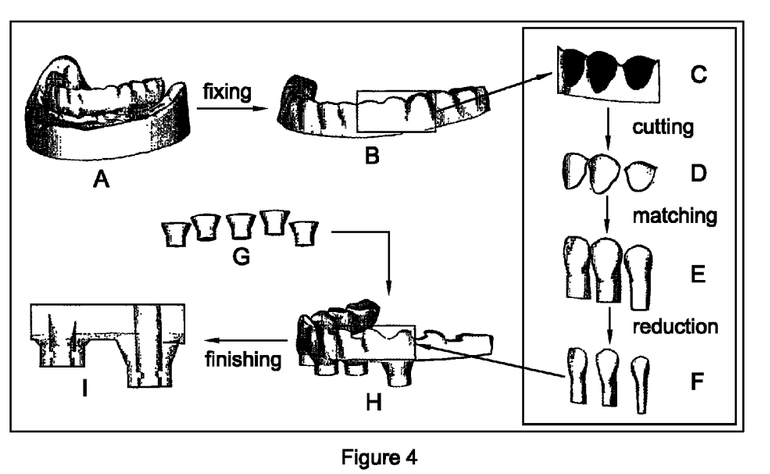
FIG. 4: Digital design strategy: (A) Measurement of the tooth arrangement upon the work model, (B) Digital 3D teeth model, (C) Identifying teeth out of teeth model, (D) Separate incomplete tooth surfaces, (E) Completed tooth surfaces after matching of corresponding standard tooth surfaces, (F) Support surfaces of framework after reduction of complete tooth surfaces, (G) Fitting structures on implant locations, (H) Designed framework as the connection of the support surfaces and the fitting structures, (I) Finishing the framework (e.g. designing holes).

The second element of the starting-geometry is the measured shape of the tooth arrangement. Preferably this measurement should not comprise deviations exceeding 0.1 mm. It can be done with a simple 3D scanner, available in most dental labs (FIG. 4a). Finally, the data on the geometry and position of the implants and remaining teeth is mathematically matched to the digitised shape of the teeth arrangement.

4. Frame Design—Step

Preferably the digital design of the framework is generated using only digital techniques and the teeth arch geometry as obtained in the measuring/mathematics step. A total design procedure was developed by defining the digital design strategy and by implementing this strategy in a software module. Several design rules were defined and put in a certain sequence to determine the digital design strategy. By translating these design rules to computer tools the design strategy was organised in a software module, which generates an automatic design of the shape of the framework.

An important element in the design step is the manipulation of the complex dataflow. The different and large data files are filtered and combined in a single geometrical model.

The design process (FIG. 4) starts with modelling the teeth arrangement based on the measurement (A). A digital 3D teeth model (B) is made by identifying the teeth arrangement out of the scan and by filling up the gaps and fixing other measurement errors like scattering and inverted normals of the surfaces. The next step is to identify each tooth out of the teeth model (C) and to cut the teeth model. Each separate tooth surface (D) is incomplete because the side surfaces of the tooth are not available in the measured 3D digital teeth model. These side surfaces are needed to calculate the reduction of the total tooth surface in order to obtain the support surface for that tooth. As indicated the teeth of the teeth arrangement are chosen out of a set of standard teeth during the preparation step. By scanning each chosen standard tooth or by selecting these teeth out of a digital library of standard teeth, a digital representation of the total surface of each individual tooth is obtained. This data allows matching each tooth in the digital 3D teeth model with a full point cloud of the corresponding standard tooth (E). In the next step the reduction can be calculated of the completed tooth surfaces in order to obtain the support surfaces of the framework (F).

The calculated data of the position of the implants (and possible remaining teeth) is transferred to the digital 3D teeth model by means of the mathematical match calculated in the previous phase. Based on this transferred data a fitting structure is placed at the position of each implant (G) (and possible remaining tooth). For the example of FIG. 4 these fitting structures are at the foot cylindrical and at the top conical. In the next step the connection is made between the fitting structures and the support surfaces of the teeth (H). In the last step the details of the framework (e.g. holes for the screws) are finished to get the final digital shape of the framework (I). Alternatively, a digital design of the framework is obtained by manually designing a physical model of the framework, using the currently applied techniques, and subsequently digitising this model. The skilled person will understand that in this approach the measuring/mathematics step is not required.

5. Production Frame—Step

A digital method to produce the framework using selective laser powder processing (SLPP) techniques, such as selective laser sintering (SLS) or selective laser full melting (SLFM) has been developed. These are rapid manufacturing techniques that use a computer controlled laser beam for scanning successive layers of powder material to create the 3D framework. Based on the slicing of the digital design (CAD-model) the scanning patterns of each layer are calculated. SLPP includes the processing of various types of powder with different types of material and different binding mechanisms can be responsible for the consolidating of the powder (see SLPP definition above and examples below). The present invention demonstrates that SLPP allows an efficient and customized production of a complex framework using different biocompatible materials (such as stainless steel, pure titanium, Ti6Al4V and CoCr) having a density above 97% and an accuracy that is medically justified. It was found that two elements were very important in achieving this accuracy, being the definition of the process parameters and the selection of the production strategy.

Process parameters: In a SLPP process a lot of process parameters have to be set (table 1). The setting of the parameters is important for getting a high precision. The process parameters can be divided into four groups: material parameters, laser parameters, scan parameters and environmental parameters A general parameter that combines different important laser and scan parameters is the energy density. This is the energy supplied by the laser beam to a unit volume of powder material. The energy density is defined by the following formula:

$$\frac{laserpower}{scanspeed \times hatchingspace \times layerthickness}$$

The energy density is an absolute process parameter and the optimal value of this parameter is independent of the type of machine, given a certain powder material. For instance the energy density for SLS using stainless steel should be within the range between 0.5 and 15 J/mm³. Using SLFM the energy density should be between 110 and 500 J/mm³, more preferably between 200 and 260 J/mm³ for titanium and between 100 and 450 J/mm³, more preferably between 170 and 230 J/mm³ for Ti6Al4V. Also using SLFM the energy density should be between 25 and 250 J/mm³, more preferably between 30 and 90 J/mm³ for CoCr.

Production strategy: The production strategy is dependent on the patient geometry and is important for fulfilling the accuracy requirements. During the definition of the production strategy geometrical decisions are taken with regard to the position of the framework within the build volume of the SLPP machine. Within the build volume the upper surfaces of a part are most accurately finished. As the fitting planes of the framework that connect with the implants should be most accurately finished it is preferred that the framework is positioned upside down in the build volume.

Figure 5:
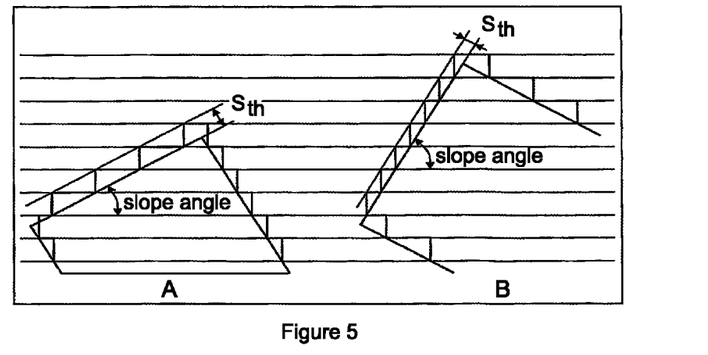
FIG. 5: The stair effect on a sloping plane due to the layer-wise production. When the slope of the plane becomes steeper the gap size $s_{th}$ becomes smaller.
Figure 6:
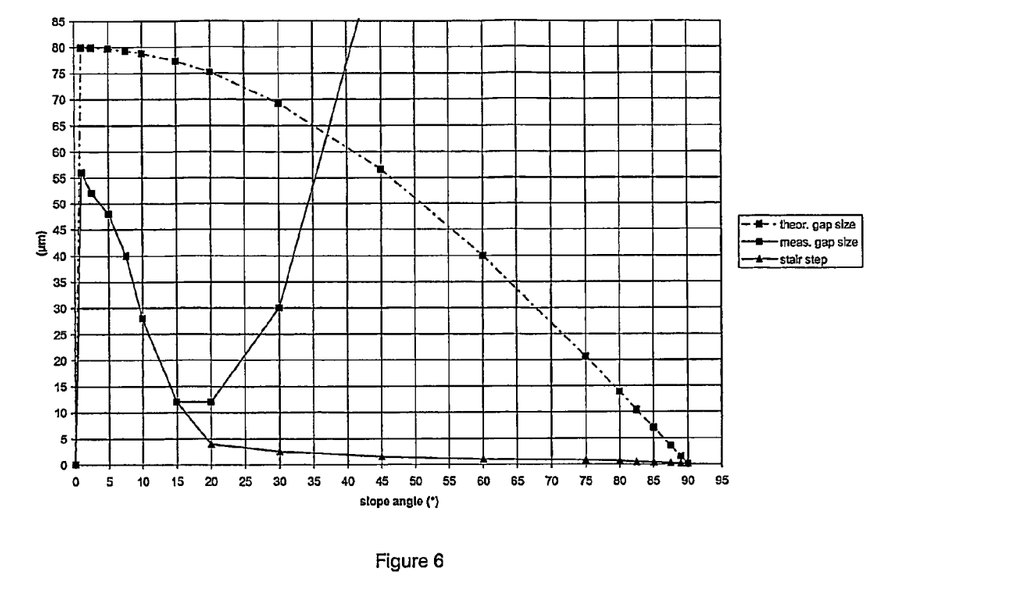
FIG. 6: Theoretical gap size, measured gap size and measured stair step versus the slope angle of the fitting plane. A minimum gap size is reached for a slope angle of 15-20°.
Figure 7:
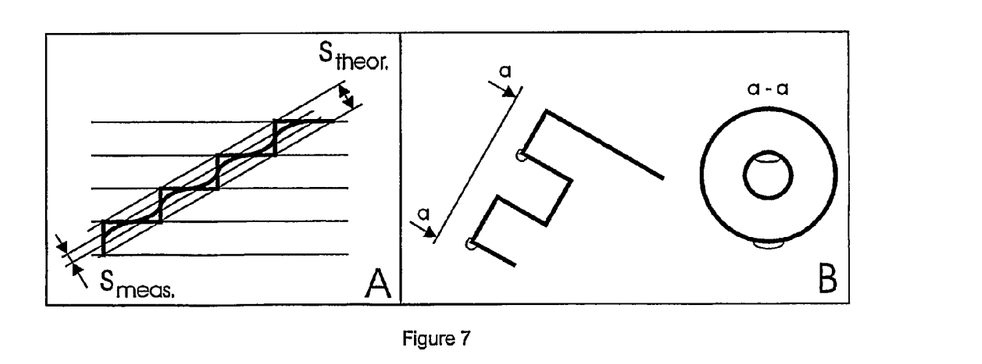
FIG. 7: (A) Because of the rounded edges of the melt pool the measured gap size is smaller than the theoretical gap size. (B) Because the laser beam interacts with more than one layer the bottom surfaces are not nicely finished and extra material is melted.

Because of the layer-wise production of the SLPP technique a stair effect appears on the sloping fitting planes of the framework (FIG. 5a). The extra material of the stair effect is attended with local inaccuracies resulting in the occurrence of gaps between the framework and the implants. Only when the fitting plane consists of a single layer of the build volume the stair effect is absent. However, the slopes of the respective fitting planes of the implants, which reflect the inclination of the implants, are different and only one fitting plane can be placed horizontally when positioning the framework in the build volume. Therefore, an optimised tilt angle under which the framework should be positioned has to be calculated taking into account the respective slopes of the fitting planes. Theoretically the gap size is proportional to the cosine of the slope angle of the fitting plane (=the angle between the fitting plane and a horizontal plane). So when the slope of the fitting plane becomes steeper, the gap size becomes smaller (FIG. 5b). This theoretical property was experimentally studied for a SLPP process by producing cylinders with a different slope in the build volume. The gap size is measured by means of a light microscope and the results are shown in FIG. 6. Up to a slope angle of 15 degrees the gap size was indeed decreasing with increasing slope angle, but the measured gap size was smaller than the theoretical gap size. This occurs because the melt pool caused by the laser interaction with the powder bed has not straight but rounded edges (FIG. 7a). When a fitting plane has a slope angle higher than 15 degrees the stair effect decreases further with increasing angle, but the total gap size increases because of other deformation phenomena. One reason is that for higher slope angles more layers are necessary and the laser has to scan the powder bed multiple times at about the same x-y position. In the ultimate case with a slope angle of ninety degrees, the laser has to scan the powder bed multiple times at exactly the same x-y position. Because the laser beam is not always perfectly at the same spot the fitting plane is not perfectly flat anymore due to the many crossings. Another extra deformation arises when for higher angles the laser is partly scanning in loose powder and, as mentioned above, bottom surfaces are not nicely finished because the laser beam interacts with more than one layer of powder. This is the reason for extra material at the bottom surfaces of the fitting plane (FIG. 7b). As a consequence of these two problems the fitting plane was not accurately finished. The fitting plane was not perfectly flat and the gap size between fitting plane and implant was higher than expected. Based on FIG. 6, the slope of the fitting planes should be around 15 degrees to minimise the errors inherent to an SLPP process. For each selective laser powder processing technique and for each material an optimal angle should be determined as described above. In the production strategy the framework is preferably positioned in the build volume in a tilted position allowing each of the fitting planes to have a slope close to the optimal angle in the build volume. For most patients the slopes of the implants don't differ more than 10 degrees and consequently it is possible to find a tilt position of the framework that optimizes the slope angles of all the fitting planes.

When using SLPP techniques, such as SLFM, which require the use of support structures, the effect of the angle of the framework in the build volume on the required size of the support structures should also be taken into account when calculating the optimal tilt angle. An important number of overhangs can be avoided by choosing an appropriate position and tilt angle for the framework in the build volume, allowing the reduction of the volume of the support structures.

Figure 8:
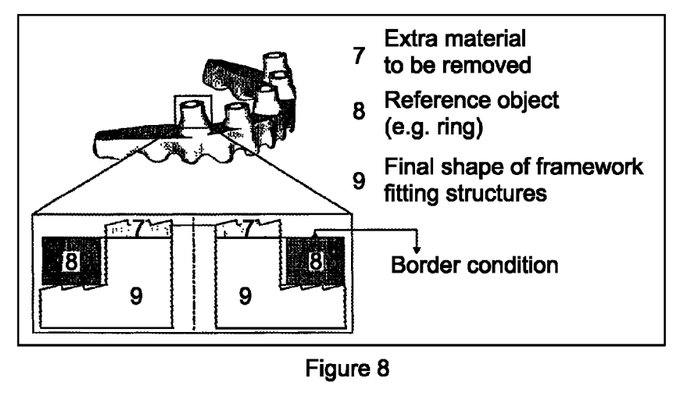
FIG. 8: The accuracy post-processing: the extra material of the fitting structure of the framework is removed by a tool. A ring is the reference object and the top surface of the ring defines the border condition of the tool path.

When applying the optimal process parameters and the proper production strategy (including the most efficient tilt angle) are not sufficient to obtain the desired accuracy, an accuracy post-processing can be applied. For instance, in case the inclination of one implant differs much from the others, the tilt operation will not succeed in reducing the stair effect enough on that implant location. Taking into account a subsequent post-processing (FIG. 8) some extra material (7) is designed upon the fitting structure of the framework, the height of this extra material being bigger than the gap size due to the stair effect. In the accuracy post-process this extra material is removed by a tool so that the fitting plane of the final shape of the framework (9) has no stair steps anymore. A known reference object (8) defines the border condition of this removal process so that the final fitting plane is on the right position. For example the top surface of a ring with well-known height defines the border of the tool path.

6. Prosthesis—Step

The final framework is post-processed by grit blasting, etching and colouring. The teeth are attached to the support surfaces of the framework by gluing or pressing. After this phase the final prosthesis is ready and can be placed in the mouth of the patient during a second medical intervention.

Figure 9:
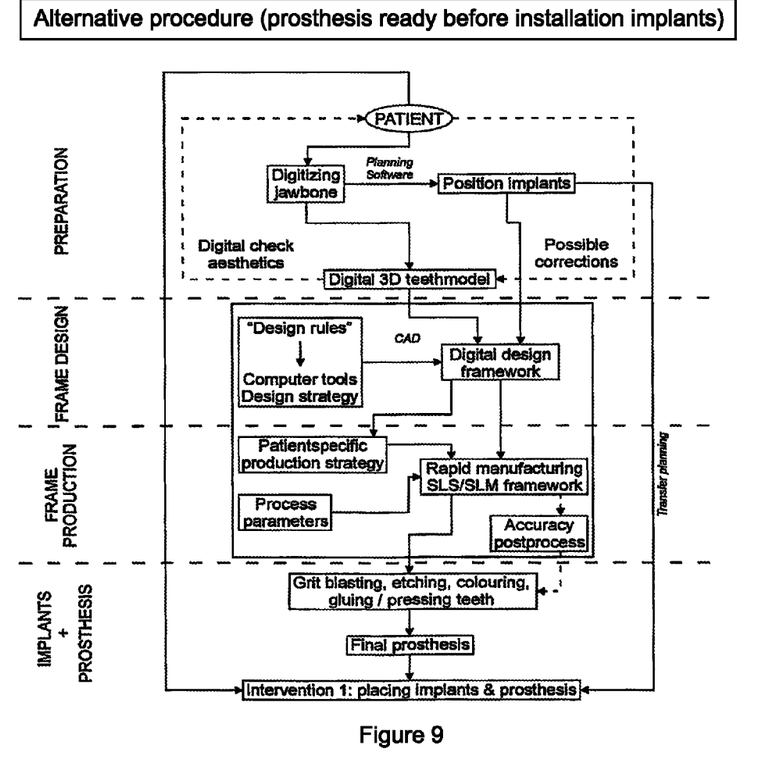
FIG. 9: Scheme representing the design and production of the framework in the Alternative procedure

B. Design and Production of a SLPP Framework in the Alternative Procedure (FIG. 9)

In contrast to the Classical procedure the Alternative procedure allows to install the implants and prosthesis in the patient's mouth during a single medical intervention. The design and production of an SLPP framework in the Alternative procedure comprises four steps termed: preparation—frame design—production frame—implants/prosthesis (FIG. 9).

1. Preparation—Step

As in the Classical procedure the positions of the implants and the type of implants are chosen in planning software using a digitized representation of the jawbone of the patient.

Also in the preparation-step a tooth arrangement is selected. Based on the CT-scans of the patient a tooth arrangement is chosen and a digital 3D teeth model is directly made on the computer. Because a physical tooth arrangement is not made in this Alternative procedure, the patient has to check the aesthetics of the tooth arrangement on the screen by means of the digital 3D teeth model.

2. Design—Step

In this Alternative procedure neither a physical tooth arrangement nor a work model is made. Because the position of the implants and the shape of the tooth arrangement are made digitally the operator can start immediately with the digital design of the framework. This is done in the same way as was described for the Classical procedure, except for the match with the standard tooth surfaces. This matching is not needed in the Alternative procedure because the tooth arrangement is made digitally and the tooth surfaces are already complete.

3. Production—Step

This step is analogous to what was described for the Classical procedure.

4. Implants/Prosthesis—Step

The final prosthesis is made by grit blasting, etching and colouring the framework and by gluing and/or pressing the teeth to the framework. Then the operator can place the implants (by means of a surgical guide) and the final prosthesis in the patient's mouth.

EXAMPLE 1

Production of a Framework in Stainless Steel Using SLPP

A framework for a certain patient was designed and produced in stainless steel by means of a SLPP process according to the method as was described for the Classical procedure.

This SLPP process makes use of stainless steel powder (diameter about 60 μm) coated by polymer material. During the SLPP process the polymer material was melted by the 100 W $CO_2$ laser and the melted polymer bound the stainless steel powder. During a furnace cycle the polymer is burned out and the green part, made by the SLPP process, is infiltrated with bronze to get a full dense framework. The laser, material, environment and scan parameters (table 1) were optimized for this SLPP process. Special attention is paid to the setting of scaling factors and offset factors to obtain high process accuracy. A general and combined process parameter is the energy density. The energy density needed for the accurate production of the framework by means of this SLPP process amounts to 1 $J/mm^3$. Taking into account this value for the energy density the most important laser and scan parameters, like layer thickness, laser power, hatching distance and scan speed, were set (see Table 2). To avoid oxidation the SLPP process is performed in a nitrogen environment.

When the final framework is fabricated, it should meet strict requirements of accuracy. As mentioned above a good passive fit with severe fit criteria between the framework and the implants is necessary. If the desired accuracy is not reached by the SLPP process, a accuracy post-processing can be applied. Several elements of the procedure are responsible for the final gap size between framework and implants:

A first neglectable error is made in the dental lab when the imprint is taken of the jaw of the patient to make the work model.

A second error is due to the measurement system. The measurement error is the accumulation of several elements: the production and mounting error of the registration elements, the use of a powder layer (needed to measure the registration elements), the resolution and/or accuracy of the measurement equipment, the calculation of the geometrical output.

The most important errors are due to the selective laser powder processing (SLPP). A first production error is the stair effect that is inherent to the layer-wise production. This stair effect can be reduced by tilting the framework in the build volume. A second production error is the point to point accuracy of the SLPP process. This process accuracy can be optimized by setting optimal process parameters. A third production error is a deformation error due to the infiltration post-process needed to get a full dense framework. Preferably this impregnation is done using a low melting biocompatible metal or alloy of Au, Ag, Pd and Pl. For a simple design this infiltration deformation is neglectable because a part with a simple geometry can be supported easily during the furnace cycle. For a complex design this infiltration deformation becomes higher because it is difficult to support the part during the furnace cycle in an adequate way. Some SLPP processes do not need a post infiltration and consequently the infiltration error doesn't exist for these SLPP processes (see example 2).

By means of different experiments it is possible to quantify the gap size accumulation of the total procedure. The gap size is divided into three errors that can be quantified:

Measurement error+ process accuracy
Stair effect
Infiltration deformation

Figure 10:
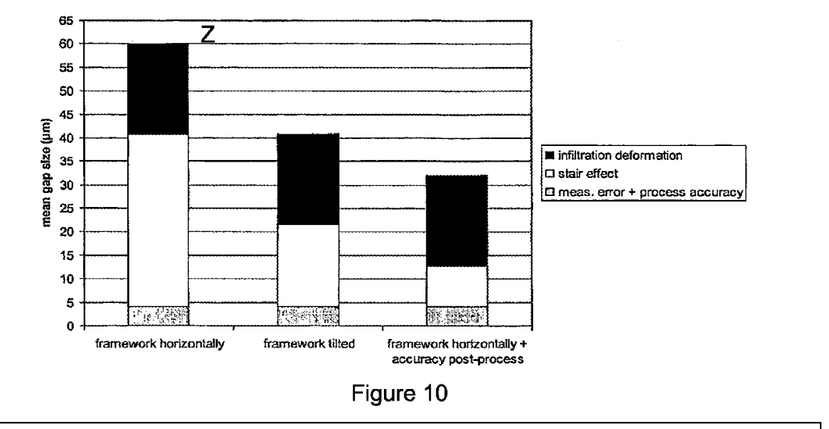
FIG. 10: Accumulation of the mean gap size for three differently produced frameworks using SLS and a nylon coated stainless steel powder.

FIG. 10 shows the diagram of the mean gap size of three produced frameworks. The gap size is divided into the three errors for each framework. The first framework is positioned horizontally in the build volume, the second framework has a tilted position in the build volume and the third framework is positioned horizontally in the build volume and has been post-processed by the accuracy post-process.

The error due to the measurement system and to the SLS process accuracy is on average 4 μm and is the same for the three frameworks. This means that the measurement procedure is very accurate.

Although the first framework is positioned in the build volume in such a way that one fitting plane is perfectly horizontally with no stair effect, the mean error due to the stair effect is very high (37 μm). This is because the absolute values of the slope angles of the other fitting planes are low (from −4° to +7°) and, as mentioned above, low slope angles give high stair effect errors. The second framework is rotated to a tilted position in the build volume. The slope angles of the fitting planes are increased (from +10° to +20°) and the mean error due to the stair effect is reduced with more than 50% (18 μm). This illustrates the importance of the positioning of the framework in the build volume under a calculated tilt angle. The third framework had a very small stair effect because a accuracy post-processing had been applied. The remaining stair effect (9 μm) was due to the fact that the accuracy post-processing was applied with a manual tool. If an automatic tool would have been used, the error due to the stair effect would have been removed.

The error due to the infiltration deformation is the same for the three frameworks (19 μm) because the shape of the frameworks is the same. This error arises because it is difficult to support the framework during the furnace cycle and no other process control can be applied.

The total mean gap size of the tilted framework is 41 μm and the total mean gap size of the post-processed framework is 32 μm.

This example 1 shows that the procedure of the present invention, including the SLPP process, allows an efficient and customized production of a complex framework with an accuracy that is medically justified.

EXAMPLE 2

Production of a Framework in a Titanium-alloy Using SLPP

The Classical procedure has been applied to fabricate a framework in a titanium-alloy, namely Ti6Al4V, for a certain patient by means of a SLPP process. This Ti6Al4V framework was designed and produced according to the method described for the Classical procedure using an SLFM process. It has good mechanical as well as geometrical properties.

In contrast to the SLPP process of example 1 this SLPP process makes use of Ti6Al4V powder (diameter about 25 μm) with no polymer or other binder material. During this SLPP process the powder material is fully melted by the 100 W Nd-YAG laser (wave length 1064 nm). The laser can be used in continuous or in pulsed mode to produce the framework and the spot size on the build platform can be changed from 100 μm to 250 μm. This SLPP process allowed to produce a fully dense framework (over 99.98% density) in one single step without the use of a post-processing or an infiltration step.

The laser, material, environment and scan parameters (table 3) were optimized for this SLPP process. A general and combined process parameter is the energy density. The energy density used in the production of the framework by means of this SLPP process was 175 $J/mm^3$. Taking into account this value for the energy density the most important laser and scan parameters, like layer thickness, laser power, hatching distance and scan speed, are set (table 3). The layer thickness could be reduced to 30 µm due to the small powder grains. To avoid oxidation of the titanium powder the SLPP process was performed in an argon environment comprising less than 0.1% oxygen. Because of thermal stresses special attention was paid to the scan parameters and scan strategy of this SLPP process to avoid deformations of the framework. Each section was divided in small sectors (about 5 mm×5 mm) and these sectors are scanned separately and successively, followed by a contour scan of the total section.

Figure 11:
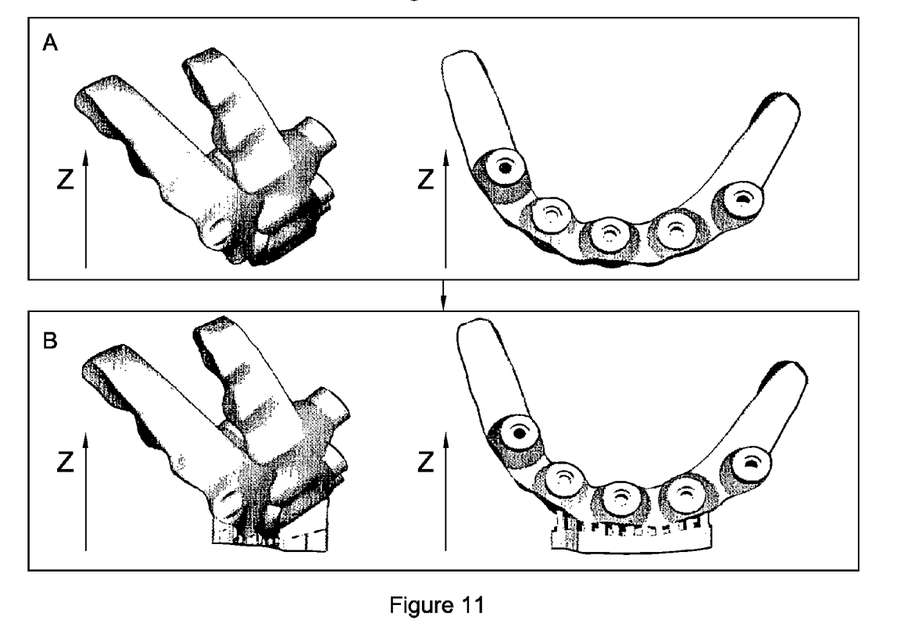
FIG. 11: Drawing of a supported and unsupported framework positioned under an appropriate tilt angle within the build volume.

For this SLPP technique a support structure was necessary to avoid low-angle (almost horizontally) overhangs. This need for support structures is taken into account in the production strategy by choosing a tilt angle for the framework in the build volume. In this way a lot of overhangs are avoided and the volume of the support structure (FIG. 11b) is reduced. By designing the connection zone between the support structure and the framework as a grid (FIG. 11b), the support structure can be removed easily from the framework. At the same time the tilted position of the framework had an advantageous effect on the stair effect.

The SLPP process is optimized with regard to the accuracy of the produced biocompatible framework to obtain a good passive fit between the framework and the implants. The accuracy of the framework was analyzed in the same way as described in example 1, by studying the gap size accumulation. The total mean gap size of the Ti6Al4V framework produced in the tilted position in the build volume was less than 25 µm.

Example 2 demonstrates that the procedure of the present invention, including the SLPP process, allows an efficient and customized production of the complex framework in a biocompatible metal (Ti6Al4V) with an accuracy that is medically acceptable.

TABLE 1

Process parameters of a SLPP process. The settings of the underlined parameters are studied to get a high precision of the framework. The other parameters are important but not changeable due to machine dependency.

| Material parameters | Laser parameters | Scan parameters | Environment parameters |
|---|---|---|---|
| Powder composition | Mode (continuous/pulsed) | Scan speed | Preheating temperature |
| Relative density | Wave-length | Scan distance | Pressure |
| Dimension distribution of grains | Power | Hatching space | Gas environment |
| Shape of grains | Frequency | Layer thickness | |
| Thermal properties | Pulse width | Scan pattern | |
| Flow properties | Offset | Scan sectors | |
| | Spot size | Scaling factors | |

TABLE 2

Process parameters of a SLS process for the production a framework using a nylon coated stainless steel powder. The legends for the different items indicated in the table can be found at the corresponding location in table 1.

| Material parameters | Laser parameters | Scan parameters | Environment parameters |
|---|---|---|---|
| Nylon coated stainless steel 316L | continuous | 1545 mm/sec | Room temperature |
| 4000 kg/m3 | 10 000 nm | Not applicable due to continuous mode | No overpressure |
| 95% smaller than 63 µm spherical | 10 W | 150 µm | Nitrogen |
| | Not applicable due to continuous mode | 80 µm | |
| Tmelt nylon = 260° C., Tmelt steel = 1500° C. | Not applicable due to continuous mode | Left to right | |
| Not viscous | 0.310 * 0.260 µm2 600 µm | none 0.987 * 1.021 * 1.098 | |

Used energy density = 10/(0.080 * 0.150 * 1545) = 0.6 J/mm3
Obtained density of part after furnace cycle was 100%

TABLE 3

Process parameters of a SLFM process for the production of a framework using a Ti6Al4V powder. The legends for the different items indicated in the table can be found at the corresponding location in table 1.

| Material parameters | Laser parameters | Scan parameters | Environment parameters |
|---|---|---|---|
| Ti6Al4V 2640 kg/m3 | continuous 1064 nm | 130 mm/sec Not applicable due to continuous mode | 30°C. No overpressure |
| 90% between 25 µm- 45 µm | 95 W | 140 µm | Argon |
| spherical | Not applicable due to continuous mode | 30 µm | |
| Tmelt = 1650° C. Cond. = 7 W/mK | Not applicable due to continuous mode | Randomized sectors, Alternating left to right, bottom to top | |
| Not viscous | 110 µm 200 µm | Islands 5 * 5 mm2 0.998 * 0.997 * 1.030 | |

Used energy density = 95/(0.030 * 0.140 * 130) = 175 J/mm3
Obtained density of part = 99.98% (almost no porosity, only few single pores)

The invention claimed is:

1. A method for the production of a dental prosthetic framework, which comprises at least two fitting structures for the installation of the framework on supporting implants and which is made of a biocompatible material having a density higher than 97%, wherein each of the fitting structures is placed at the position of the implant, wherein the framework is directly produced using a layer-wise selective laser powder processing (SLPP) technique, the method comprising the steps of:
   determining an empirically optimal angle to minimize errors related to layer-wise production;
   positioning the framework under a tilt angle so that a slope of at least one fitting plane of the at least two fitting structures forms an angle in a build volume with a plane having the empirically optimal angle, wherein the framework is positioned so that if possible all of the angles of the fitting planes differ less than 10° from the empirically optimal angle;
   when at least one of the fitting planes has a slope having an angle in the build volume differing more than 10° from the empirically determined optimal angle, designing and producing the respective at least one of the fitting structures to include extra material extending the respective at least one of the fitting structures, wherein the height of this extra material is bigger than a gap size due to a stair effect; and subjecting said fitting structures including said extra material to a post processing step during which said extra material is removed by a tool to obtain a final framework shape which is free of the stair effect.

2. The method according to claim 1 wherein said biocompatible material has a density higher than 99%.

3. The method according to claim 1 wherein the biocompatible material is pure titanium, a titanium-alloy, a cobalt-chromium-alloy or a ceramic.

4. The method according to claim 1 comprising:
   (i) obtaining a digital model of the framework,
   (ii) producing the framework according to said digital model using a selective laser powder processing technique.

5. The method according to claim 1, said method comprising:
   (i) obtaining a digital model of the framework,
   (ii) defining a production strategy determining the position of the framework within the build volume of the SLPP machine taking into account the respective slopes of the fitting planes of the fitting structures,
   (iii) producing the framework according to said digital model and said production strategy using a selective laser powder processing technique.

6. The method according to claim 4 or 5 wherein the digital model of the framework is obtained by manually designing a physical model of the framework and subsequently digitizing said physical model.

7. The method according to claim 4 wherein the digital model of the framework is obtained by
   (i) obtaining the teeth arch geometry, which comprises digital data on (a) the position and geometry of each implant and remaining tooth, on (b) the shape of the teeth arrangement (c) on the calculated match between said elements, and
   (ii) designing the digital model of the framework using said teeth arch geometry.

8. The method according to claim 7 wherein the determination of the teeth arch geometry comprises following steps:
   (i) measuring the position and geometry of each implant and remaining tooth on a physical work model of the patient's jaw bone, said work model being prepared after the installation of the implants in the patient's mouth,
   (ii) preparing a physical teeth arrangement on said work model,
   (iii) digitising said physical teeth arrangement to obtain a digital 3D teeth model; and
   (iv) mathematically matching the measurements obtained in step (i) and (iii).

9. The method according to claim 7 wherein the determination of the teeth arch geometry comprises the following steps
   (i) planning the installation of the implants in the patient's jawbone using a digitised representation of the jawbone and appropriate planning software,
   (ii) generating a digital 3D teeth model by selecting and positioning virtual teeth on the digitised representation of the jawbone,
   (iii) deriving the teeth arch geometry out of the digital data generated in steps (i) and (ii).

10. A method according to any of claims 7 to 9 wherein the design of the digital model of the framework comprises following steps
    (i) obtaining a digital representation of the total tooth surface of each tooth comprised in the digital 3D teeth model,
    (ii) calculating a reduction of each tooth surface comprised in the 3D digital teeth model in order to determine the geometry of the surfaces required on the framework to support the respective teeth,
    (iii) designing the fitting structures on the digital framework using the data on the positions and geometries of the implants and remaining teeth, and
    (iv) designing the connection between the designed fitting structures and the in step (ii) calculated support surfaces, using the calculated match between the two elements of the teeth arch geometry.

11. The method according to claim 4 wherein the framework is positioned in the build volume of the production device with the fitting planes oriented upwards.

12. The method according to claim 4 wherein the SLPP technique is selective laser sintering.

13. The method according to claim 4 wherein the SLPP technique is selective laser full melting.

14. The method according to claim 4 wherein the SLPP technique is selective laser cladding.

15. The method according to claim 1 wherein horizontal bottom planes of the framework, said bottom planes being parallel to the basis of the building platform, and overhanging planes of the framework, which connect to these horizontal bottom planes with an angle below 30°, are supported by support structures linking said bottom and overhanging planes with the basis of the building platform.

16. The method according to claim 15 wherein the support structures connect with the supported planes of the framework via a grid structure.

17. The method according to claim 15 or 16 wherein the selective laser processing technique is selective laser full melting or selective laser cladding.

18. A method for the production of a dental prosthetic framework, which comprises at least two fitting structures for screw fixing the framework on supporting implants, wherein each of said fitting structures is placed at the position of an implant, and which is made of a biocompatible material having a density higher than 97%, the method comprising the step of directly producing said framework using a selective laser powder processing technique;
    wherein the method further comprises the steps of:
    calculating an optimized tilt angle under which the framework should be positioned during said step of producing the framework taking into account the respective slopes of the fitting planes; and
    positioning the framework in the build volume in a tilted position allowing each of the fitting planes to have a slope close to the calculated optimized tilt angle.

19. The method according to claim 1, wherein the framework is positioned so that if possible all of the angles of the fitting planes differ less than 5° from the empirically optimal angle, and when at least one of the fitting planes has a slope having an angle in the build volume of more than 5° from the empirically optimal angle, the extra material is included to extend beyond the respective fitting plane of at least one fitting structure.

* * * * *